(12) United States Patent
Schilling et al.

(10) Patent No.: US 8,883,468 B2
(45) Date of Patent: Nov. 11, 2014

(54) 1-HYDROXY-OCTAHYDROAZULENES AS FRAGRANCES

(75) Inventors: Boris Schilling, Knonau (CH); Thierry Granier, Duebendorf (CH); Esther Locher, Dubendorf (CH)

(73) Assignee: Givaudan S.A., Vernier (CH)

( * ) Notice: Subject to any disclaimer, the term of this patent is extended or adjusted under 35 U.S.C. 154(b) by 54 days.

(21) Appl. No.: 13/703,761

(22) PCT Filed: Jun. 28, 2011

(86) PCT No.: PCT/EP2011/060862
§ 371 (c)(1),
(2), (4) Date: Dec. 12, 2012

(87) PCT Pub. No.: WO2012/001018
PCT Pub. Date: Jan. 5, 2012

(65) Prior Publication Data
US 2013/0089904 A1    Apr. 11, 2013

(30) Foreign Application Priority Data

Jun. 29, 2010    (EP) .................................... 10167739

(51) Int. Cl.
| C11B 9/00 | (2006.01) |
| A23L 1/222 | (2006.01) |
| A23L 1/226 | (2006.01) |
| C07C 35/34 | (2006.01) |
| C12P 7/02 | (2006.01) |

(52) U.S. Cl.
CPC ........... *C11B 9/0049* (2013.01); *C07B 2200/07* (2013.01); *A23L 1/2265* (2013.01); *A23L 1/222* (2013.01); *C07C 35/34* (2013.01); *C07C 2102/26* (2013.01); *C12P 7/02* (2013.01)
USPC ............ 435/155; 568/819; 512/19; 426/538; 426/442

(58) Field of Classification Search
CPC .............................. C11B 9/0049; A23L 1/222
USPC ............ 435/155; 568/819; 512/19; 426/538, 426/442
See application file for complete search history.

(56) References Cited

FOREIGN PATENT DOCUMENTS

JP    4077444 A    3/1992

OTHER PUBLICATIONS

PCT/EP2011/060862—International Search Report, Aug. 29, 2011.
PCT/EP2011/060862—International Written Opinion, Aug. 29, 2011.
Ishihara M. et al.; "Three Sesquiterpenes from Agarwood"; Phytochemistry, vol. 30, No. 2. pp. 563-566, 1991, Pergamon Press.
Shono, Tatsuya, et al. "Electroorganic Chemistry, 140, Electroreductively Promoted Intra-and-Intermolecular Couplings of Ketones with Nitriles"; Journal of Organic Chemistry, 1992, vol. 57, No. 26, pp. 7175-7187.
EP10167739.1—European Search Report, Dec. 2, 2010.

*Primary Examiner* — Chih-Min Kam
(74) *Attorney, Agent, or Firm* — Curatolo Sidoti Co., LPA; Joseph G. Curatolo; Salvatore A. Sidoti

(57) ABSTRACT

(3S,5R)-3,8-dimethyl-5-(prop-1-en-2-yl)-octahydroazulen-1-ols, their use as flavor or fragrance ingredient, and a process of their production by oxidation in the presence of laccase.

10 Claims, No Drawings

1-HYDROXY-OCTAHYDROAZULENES AS FRAGRANCES

CROSS REFERENCE TO RELATED APPLICATIONS

This application is a national stage application of International Application No. PCT/EP2011/060862, filed 28 Jun. 2011, which claims priority from European Patent Application No. 10167739.1, filed 29 Jun. 2010, from which applications priority is claimed, and which are incorporated herein by reference.

The present invention refers to (3S,5R)-3,8-dimethyl-5-(prop-1-en-2-yl)-octahydroazulen-1-ols and their use as flavour or fragrance ingredient. The invention relates furthermore to a process of their production and to consumer products comprising it.

In the flavour and fragrance industry there is a constant demand for compounds possessing unique olfactory properties, in particular floral, woody odour notes. Such compounds extend a perfumer's palette and result in greater product diversity for consumers.

We have now found a novel class of octahydroazulenol derivatives that possess very strong floral, woody odour characteristics.

Accordingly, in a first aspect, there is provided the use as flavour or fragrance of a compound of formula (I)

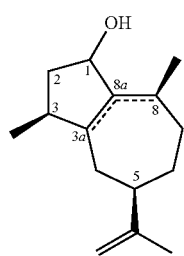

(I)

wherein the dotted line together with the carbon-carbon bond between C-3a and C-8a represents a double bond and the dotted line together with carbon-carbon bond between C-8a and C-8 represents a single bond; or
the dotted line together with the carbon-carbon bond between C-8 and C-8a represents a double bond and the dotted line together with carbon-carbon bond between C-3a and C-8a represents a single bond, and C-3a is (S)-configurated.

The compounds of formula (I) may be used alone, as mixtures thereof, or in combination with a base material. As used herein, the "base material" includes all known flavour and odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with flavours/odorants in flavour and fragrance compositions, for example, carrier materials, and other auxiliary agents commonly used in the art.

As used herein, "flavour/fragrance composition" means any composition comprising at least one compound of formula (I) and a base material, e.g. a diluent conventionally used in conjunction with flavours/odorants, such as dipropylene glycol (DPG), isopropyl myristate (IPM), triethyl citrate (TEC), alcohol (e.g. ethanol), propylene glycol (PG), triacetine, and benzylic alcohol, and/or a known flavour or odorant.

The following list comprises examples of known odorant molecules, which may be combined with the compounds of formula (I):

essential oils and extracts, e.g. castoreum, costus root oil, oak moss absolute, geranium oil, tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;

alcohols, e.g. cinnamic alcohol, cis-3-hexenol, citronellol, Ebanol™ (3-methyl-5-(2,2,3-trimethyl-3-cyclopenten-1-yl)-4-penten-2-ol), eugenol, farnesol, geraniol, Super Muguet™ (6-ethyl-3-methyl-5(6)-octen-1-ol), linalool, menthol, nerol, phenylethyl alcohol, rhodinol, Sandalore™ (5-(2,2,3-trimethyl-3-cyclopentyl)-3-methylpentan-2-ol), terpineol or Timberol™;

aldehydes and ketones, e.g. Azurone® (7-(3-methylbutyl)-1,5-benzodioxepin-3-one), anisaldehyde, α-amylcinnamaldehyde, Georgywood™ (2-acetyl-1,2,3,4,5,6,7,8-octahydro-1,2,8,8-tetramethylnaphthalene), hydroxycitronellal, Iso E® Super, Isoraldeine®, Hedione®, Lilial®, maltol, methyl cedryl ketone, methylionone, rotundone, verbenone or vanillin;

ethers and acetals, e.g. Ambrox™, geranyl methyl ether, rose oxide or Spirambrene™ ((1R,3S,6S)-rel-2',2',3,7,7-pentamethyl-spiro[bicyclo[4.1.0]heptane-2,5'-[1,3]dioxane]);

esters and lactones, e.g. benzyl acetate, Cedryl acetate, γ-decalactone, Helvetolide®, γ-undecalactone or vetivenyl acetate;

macrocycles, e.g. Ambrettolide, ethylene brassylate or Exaltolide®;

heterocycles, e.g. isobutylquinoline.

Whereas the compounds of formula (I) possessing a very pleasant organoleptic characteristic in its own right they are particular suitable when combined with a compound selected from (3S,5R,8S)-3,4,5,6,7,8-hexahydro-3,8-dimethyl-5-(1-methylethenyl)-1(2H)-azulenone (Rotundone); 3,4,5,6,7,8-hexahydro-3,8,9,9-tetramethyl-5,8-methanoazulen-1(2H)-one (also known as 1,4,5,6,7,8-hexahydro-1,4,9,9-tetramethyl-4,7-methanoazulen-3(2H)-one, or β-Patchoulenone) and its corresponding alcohols (1,2,3,4,5,6,7,8-octahydro-1,4,9,9-tetramethyl-4,7-methanoazulen-3(2H)-ols); Caryophyllene oxide ((1R,4R,6R,10S)-4,12,12-trimethyl-9-methylene-5-oxatricyclo[8.2.0.04,6]dodecane); and [3S-(3α,3aβ,5α)]-3,3a,4,5,6,7-hexahydro-3,8-dimethyl-5-(1-methylethenyl)-1(2H)-azulenone (also known as (3S,3aS,5R)-3,8-dimethyl-5-(prop-1-en-2-yl)-3,3a,4,5,6,7-hexahydroazulen-1(2H)-one and described below as α-Bulnesenone).

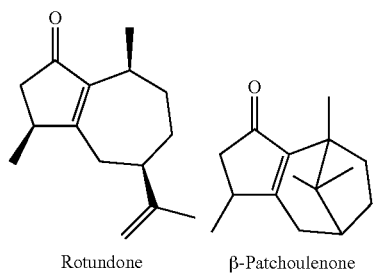

Rotundone β-Patchoulenone

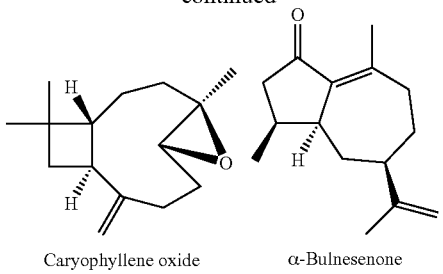

Caryophyllene oxide    α-Bulnesenone

The compounds according to formula (I) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odorant ingredients. The proportion is typically from 0.001 to 20 weight percent of the application. In one embodiment, compounds of the present invention may be employed in a fabric softener in an amount of from 0.01 to 5 weight percent. In another embodiment, compounds of the present invention may be used in fine perfumery in amounts from 0.005 to 10 weight percent (e.g. up to about 2 weight percent), more preferably between 0.01 and 5 weight percent. However, these values are given only by way of example, since the experienced perfumer may also achieve effects or may create novel accords with lower or higher concentrations.

In a further embodiment, the compounds of formula (I) may also be used as flavour ingredient in a broad range of flavour applications, including alcoholic and non-alcoholic beverages, e.g. teas, frozen diary desserts, confectionary and bakery goods, gelatines, puddings, meat and meat products, and tobacco. The compounds of formula (I) may also be used as flavour ingredient for flavour compositions, for example, in grape flavours, plum flavours, dried fruit flavours, red berry flavours such as raspberry, blackberry or gooseberry flavours. They may also be used as flavour enhancers, for example, in pepper, ginger, basil, rosemary, cardamom, nutmeg, cinnamon, peppermint, grape (such as Shiraz grape), juniper and grapefruit flavours.

When used in flavour applications, the compounds of the present invention may be present in amounts ranging from 0.01 ppb ($10^{-11}$) to 10 ppb ($10^{-8}$) by weight based on the consumable product, more preferably from 0.1 ppb ($10^{-10}$) to 1 ppb ($10^{-9}$) by weight. However, these values should not be limiting on the present invention, since the experienced flavourist may also achieve effects or may create novel accords with lower or higher concentrations.

The compounds as described hereinabove may be employed in a consumer product base simply by directly mixing at least one compound of formula (I), or a composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof. The compounds of formula (I) may be dissolved or dispersed in a carrier material, such as a fat, or enrobed with maltose-dextrin, gelatine, gum Arabic and the like. They may be mixed with the ingredients ready to be prepared or mixed with one of the ingredients, and then mixed with the product base.

In a further aspect the compounds of formula (I) may be chemically bonded to substrates, which are adapted to release the molecule upon application of an external stimulus such as light, enzyme, temperature, moister, or the like, and then mixed with the product base.

Thus, the invention additionally provides a method of manufacturing a flavour or fragrance application, comprising the incorporation of a compound of formula (I), either by directly admixing the compound to the consumer product base or by admixing a flavour/fragrance composition comprising a compound of formula (I), which may then be mixed with a consumer product base, using conventional techniques and methods. Through the addition of an organolepticly acceptable amount of at least one compound of formula (I) as defined above the aroma of a consumer product base will be improved, enhanced, or modified.

Thus, the invention furthermore provides a method for improving, enhancing or modifying a consumer product base by means of the addition thereto of an organolepticly acceptable amount of at least one compound of formula (I).

The invention also provides a flavour or fragrance application comprising:

a) as odorant/flavour at least one compound of formula (I); and b) a consumer product base.

As used herein, "consumer product base" means a composition for use as a consumable product or a consumer product. By "consumer product" is meant any product which fulfils specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing creme. This list of products is given by way of illustration and is not to be regarded as being in any way limiting.

By "consumable product" is meant a product such as foodstuffs and beverages, or personal care products that are intended to be introduced into the oral cavity of a human or animal and remain there for a certain period of time before being ingested or removed from the mouth. Such products include compositions in their processed, partially processed or unprocessed state.

The compounds of formula (I) wherein the dotted line together with the carbon-carbon bond between C-8 and C-8a represents a single bond and the dotted line together with carbon-carbon bond between C-3a and C-8a represents a double bond may be synthesized by reduction of rotundone in the presence of hydrides (e.g. LiAlH$_4$, NaBH$_4$, and the like) under conditions known to the person skilled in the art.

Compounds of formula (I) wherein the dotted line together with the carbon-carbon bond between C-3a and C-8a represents a single bond and the dotted line together with carbon-carbon bond between C-8a and C-8 represents a double bond may be synthesized by reduction of α-bulnesenone ([3S-(3α, 3aβ,5α)]-3,3a,4,5,6,7-hexahydro-3,8-dimethyl-5-(1-methylethenyl)-1(2H)-azulenone).

Alternatively, the compounds of formula (I) may be synthesized by oxidation of α-guaiene and/or α-bulnesene in the presence of laccase, a process which according to our best knowledge has not been suggested before.

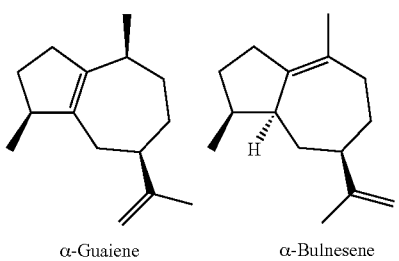

α-Guaiene    α-Bulnesene

Accordingly, in one embodiment there is provided a process comprising the step of reacting laccase and a compound selected from α-guaiene and α-bulnesene in the presence of an oxygen source.

In a further embodiment there is provided a process for the production of compounds of formula (I) wherein the dotted line together with the carbon-carbon bond between C-8 and C-8a represents a single bond and the dotted line together with carbon-carbon bond between C-3a and C-8a represents a double bond comprising the step of reacting α-guaiene and laccase in the presence of an oxygen source.

In a further embodiment there is provided a process for the production of compounds of formula (I) wherein the dotted line together with the carbon-carbon bond between C-3a and C-8a represents a single bond and the dotted line together with carbon-carbon bond between C-8 and C-8a represents a double bond comprising the step of reacting α-bulnesene and laccase in the presence of an oxygen source One may use the neat α-guaiene and/or α-bulnesene as starting material ore one may use a material, preferably of natural origin, comprising said compounds such as patchouli oil.

Patchouli oil is obtained by steam distillation from the, preferably dried and optionally fermented, leaves and stems of *Pogostemon cablin* Benth, belonging to the family Labiateae. It has been used for centuries in perfumes and continues to be so today. The composition of the oil may vary, depending on several factors, including the cultivar grown, the cultivation and harvesting regimes, drying and storage practise for the leaf.

Instead of using patchouli oil as a starting material one may use a light fraction of patchouli oil. By "light fraction of patchouli oil" is meant in the present context the volatile fraction obtained by distillation of patchouli oil that contains the sesquiterpenic olefins of the oil. In one embodiment the light fraction is enriched in α-guaiene and/or α-bulnesene. In another embodiment the light fraction of the patchouli oil is essentially free of patchouli alcohol (CAS 5986-55-0). By "essentially free" is meant a patchouli oil fraction comprising less than 2% patchouli alcohol, preferably less than 1% by weight based on the used fraction.

The fraction of patchouli oil essentially free of patchouli alcohol is preferably used because patchouli alcohol is of high perfumery interest when taken alone.

To be of commercial interest for the production of compounds of formula (I) as defined above the patchouli oil comprises at least 0.05 weight % (e.g. at least 0.1 to about 1 weight %) of α-guaiene and/or α-bulnesene based on the used fraction. Preferably, at least one of the two compounds is present in amounts up to about 50 weight % or even higher, e.g. the patchouli oil or a light fraction thereof comprises about 15-70% by weight of α-bulnesene based on the used fraction, or e.g. the patchouli oil or a light fraction thereof comprises about 15-50% by weight of α-guaiene based on the used fraction.

Thus, in a further aspect the invention refers to a process for the production of a compound of formula (I) as defined above by enzymatic oxidation of patchouli oil or a light fraction thereof.

In a further aspect the invention refers to a process comprising the step of reacting patchouli oil or a light fraction thereof and laccase in the presence of an oxygen source.

In a further aspect a mixture of patchouli oil or a light fraction thereof with an aqueous phase in a ration of 1:10 to 10:1, including an ratio of 1:9, 1:4, 1:3 and 5:1, is used for the enzymatic oxidation.

Laccase is used to catalyze the oxidation of the lower olefins constituting a major part of compounds in patchouli oil, and the most part the light fraction thereof, in particular α-guaiene and α-bulnesene respectively. Laccase from a microbial sources, as well as laccase purchased from commercial vendors and/or generated using recombinant techniques, could be used in either a reaction composition or in an immobilized form. One or more mediators and/or solvent (e.g. DPG) at a concentration to maintain laccase activity could also be added.

The microbial laccase may be derived from bacteria or fungi (including filamentous fungi and yeasts) and suitable examples include a laccase derivable from a strain of *Aspergillus, Neurospora*, e.g. *N. crassa, Podospora, Botrytis, Collybia, Fomes, Lentinus, Lentinus, Pleurotus, Trametes, Rhizoctonia*, e.g. *R. solani, Coprinus*, e.g. *C. plicatilis, Psatyrella, Myceliophtera*, e.g. *M. thermophila, Schytalidium*, and *Polyporus*, e.g. *P. pinsitus, Phiebia*, or *Coriolus*.

The laccase may be in any form, e.g. in the form of a dry powder, or granulate, a liquid, in particular a stabilized liquid, or a protected enzyme. The enzyme can be immobilized, or contained in particles, such as capsules where substrates and products can freely diffuse between the reservoir and the enzyme.

A mediator as used herein is defined as a diffusible molecule that is activated by an oxidative enzyme and diffuses from the active site on the enzyme to a susceptible structure. While laccase can function as a catalyst independently, it is known that the presence of certain mediators may enhance the laccase-catalyzed reaction. The following chemicals have been found to be active as mediators: 1-hydroxybenzotriazole (HBT), 2,2'-azino-bis(3-ehylbenzthiazoline-6-sulfonic acid (ABTS), ferulic acid, dimethyoxy benzyl alcohol, dimethamino benzoic acid, catechin, epicatechin, p-hydroxyphenylacetic acid, quercetin, chloropromazine, phenothiazine, naringin, promazine, homovanillic acid, 4-amino-salicylic acid, syringic acid, methyl syringate, 4-hydroxycinnamic acid, 4-amino-3-hydroxybenzoic acid, vanillic acid, isovanillic acid, caffeic acid, α-resorcylic acid, β-resorcylic acid, γ-resorcylic acid, 2,3-dihydroxybenzoic acid, 3,4-dihydroxybenzoic acid, 4-hydroxybenzoic acid, 3-hydroxybenoic acid, 2,4,6-trihydroxybenzoic acid, benzoic acid, cinnamic acid, sodium benzoate, salicylic acid, acetosyringone, and violuric acid. It will be recognized by one skilled in the art that other related chemicals might also be useful as mediators. One or more mediators may be included at a concentration up to about 50 mM, preferably at a concentration greater than 0.1 mM and up to about 5 mM, to enhance the reaction.

The oxygen source may be pure oxygen or a mixture of gases containing oxygen, such as air or other gas mixtures.

The oxidation in the presence of laccase may proceed for any length of time, for example up to one week or longer, but reacting for at least about 2 days produced commercially viable quantities.

In one embodiment the reaction occurred about 70 hours at about 40° C. at and at a pH in the range of pH 7.6-5.2. The reaction was stopped by raising the pH of the reaction broth to pH 12 with NaOH and heating to at least 95° and $N_2$-bubbling through the reaction mixture for at least 8 hours.

When the reaction products are used as flavour, food grade starting materials are used, for example, food grade laccase as offered for example under the trade name Suberase® by Novozymes.

The invention is now further described with reference to the following non-limiting examples. These examples are for the purpose of illustration only and it is understood that variations and modifications can be made by one skilled in the art.

EXAMPLE 1

(1R,3S,5R,8S)- and (1S,3S,5R,8S)-3,8-dimethyl-5-(prop-1-en-2-yl)-1,2,3,4,5,6,7,8-octahydroazulen-1-ol At −70° C., a suspension of lithium aluminium hydride (0.52 g, 13.7 mmol) in diethyl ether (30 ml) was treated dropwise within 10 min. with a solution of (−)-rotundone ((3S,5R,8S)-3,4,5,6,7,8-hexahydro-3,8-dimethyl-5-(1-methylethenyl)-1(2H)-azulenone; 3.0 g, 13.7 mmol) in diethyl ether (20 ml). The resulting mixture was stirred for 1 h at −70° C., treated dropwise with a 2M aqueous NaOH solution (2.5 ml) while the reaction temperature rose to −20° C., stirred for 20 min., treated with $MgSO_4$ (5 g), stirred for 10 min., filtered, and the solvent evaporated. Flash chromatography (400 g 0.015-0.040 mm-$SiO_2$, flow: 80 ml/min., hexane/methyl t-butyl ether 100:0 to 85:15 in 30 min.) of the crude product (2.8 g, GC: 65:35 (1R)/(1S)-epimer) gave (1R,3S,5R,8S)-3,8-dimethyl-5-(prop-1-en-2-yl)-1,2,3,4,5,6,7,8-octahydroazulen-1-ol (1.07 g, 35%) and (1S,3S,5R,8S)-3,8-dimethyl-5-(prop-1-en-2-yl)-1,2,3,4,5,6,7,8-octahydroazulen-1-ol (0.64 g, 21%).

a) (1R,3S,5R,8S)-3,8-dimethyl-5-(prop-1-en-2-yl)-1,2,3,4,5,6,7,8-octahydroazulen-1-ol Boiling point: 120° C. (0.06 mbar).
$^1$H-NMR (400 MHz, $C_6D_6$): δ 4.80-4.78 (br. s, H—C(1')), 4.73 (quint, J=1.5, H—C(1')), 4.43-4.36 (m, H—C(1)), 2.56-2.47 (m, H—C(8)), 2.36-2.23 (m, H—C(4), H—C(2), H—C(3)), 2.05 (dt, J=2.0, 15.2, H—C(4)), 1.94 (tm, J=2.0, 11.4, H—C(5)), 1.90-1.80 (m, H—C(6)), 1.77-1.70 (m, H—C(6)), 1.65 (dd, J=0.9, 1.4, C(1')$H_3$), 1.63-1.49 (m, C(7)$H_2$), 1.22 (d, J=7.1, MeC(8)), 1.17-11.10 (m, H—C(2)), 0.97 (d, J=6.8, MeC(3)).
$^{13}$C-NMR (125 MHz, $C_6D_6$): δ 152.10 (s, C(2')), 144.40 (s, C(8a)), 142.80 (s, C(3a)), 108.70 (t, C(1')), 80.90 (d, C(1)), 46.90 (d, C(5)), 42.90 (d, C(3)), 42.20 (t, C(2)), 34.00 (t, C(4)), 33.90 (t, C(7)), 32.00 (d, C(8)), 31.50 (t, C(6)), 21.10 (q, MeC(3)), 20.40 (q, C(3')), 19.20 (q, MeC(8)).
MS (EI): 220 (9), 203 (10), 202 (51), 187 (41), 173 (11), 164 (13), 163 (41), 160 (16), 159 (57), 147 (25), 146 (36), 145 (96), 133 (27), 132 (17), 131 (65), 121 (35), 120 (30), 119 (77), 117 (28), 115 (23), 109 (23), 108 (21), 107 (34), 106 (23), 105 (100), 95 (36), 93 (49), 91 (85), 81 (23), 79 (42), 77 (45), 69 (17), 67 (29), 65 (20), 55 (34), 53 (24), 41 (42).
$[α]_D^{22}$=−55.8 (1.06 in EtOH)
Odour description: floral, resinous, tobacco, spicy, peppery, woody.

b) (1S,3S,5R,8S)-3,8-dimethyl-5-(prop-1-en-2-yl)-1,2,3,4,5,6,7,8-octahydroazulen-1-ol Boiling point: 120° C. (0.06 mbar).
$^1$H-NMR (400 MHz, $C_6D_6$): δ 4.82-4.78 (br. s, H—C(1')), 4.75-4.73 (br. m, H—C(1')), 4.61-4.56 (m, H—C(1)), 2.71-2.62 (m, H—C(8)), 2.58-2.49 (br. m, H—C(3)), 2.23-2.11 (m, H—C(4), H—C(5)), 2.01 (d, J=12.9, H—C(4)), 1.82 (ddd, J=4.1, 7.8, 13.4, H—C(2)), 1.77-1.59 (m, C(6)$H_2$, C(7)$H_2$, H—C(2)), 1.65 (dd, J=0.8, 1.3, C(1')$H_3$), 1.01 (d, J=7.1, MeC(8)), 0.85 (d, J=7.1, MeC(3)).
$^{13}$C-NMR (125 MHz, $C_6D_6$): δ 151.80 (s, C(2')), 144.10 (s, C(8a)), 143.00 (s, C(3a)), 108.80 (t, C(1')), 78.70 (d, C(1)), 46.90 (d, C(5)), 43.40 (d, C(3)), 42.70 (t, C(2)), 34.40 (t, C(7)), 34.10 (t, C(4)), 31.40 (t, C(6)), 30.50 (d, C(8)), 20.50 (q, MeC(3)), 20.40 (q, C(3')), 18.00 (q, MeC(8)).
MS (EI): 220 (6), 203 (10), 202 (56), 187 (39), 173 (11), 164 (8), 163 (31), 160 (17), 159 (64), 147 (24), 146 (43), 145 (100), 133 (28), 132 (18), 131 (68), 121 (28), 120 (27), 119 (71), 117 (30), 115 (25), 109 (16), 108 (17), 107 (28), 106 (23), 105 (99), 95 (27), 93 (45), 91 (84), 81 (19), 79 (38), 77 (43), 69 (13), 67 (24), 65 (20), 55 (29), 53 (23), 41 (38).
$[α]_D^{22}$=−73.9 (0.95 in EtOH)
Odour description: floral, rosy, woody.

EXAMPLE 2

(1R,3S,3aS,5R)- and (1S,3S,3aS,5R)-3,8-dimethyl-5-(prop-1-en-2-yl)-1,2,3,3a,4,5,6,7-octahydroazulen-1-ol via (3S,3aS,5R)-3,8-dimethyl-5-(prop-1-en-2-yl)-3,3a,4,5,6,7-hexahydroazulen-1(2H)-one A) (3S,3aS,5R)-3,8-dimethyl-5-(prop-1-en-2-yl)-3,3a,4,5,6,7-hexahydroazulen-1(2H)-one At −30° C., a solution of 3,5-dimethyl-1H-pyrazole (7.2 g, 74.9 mmol) in dichloromethane (40 ml) was treated with $CrO_3$ (7.5 g, 74.9 mmol, added in two portions) while the reaction temperature rose to −20° C. The resulting mixture was stirred at −20° C. for 0.5 h and treated within 20 min. with a solution of α-bulnesene (3.0 g, 14.7 mmol) in dichloromethane (20 ml) while the reaction temperature rose to −10° C. The resulting mixture was stirred between −20° C. and −10° C. for 4 h before allowing the reaction temperature to slowly reach 20° C. (overnight), treated with 8M aqueous NaOH (70 ml), stirred at 20° C. for 20 h, and extracted with MTBE (400 ml). The aqueous phase was extracted with MTBE (150 ml) and the joined organic phases were washed twice with 2 M aq. HCl (100 ml), once with $H_2O$ (100 ml), once with aqueous saturated NaCl solution (100 ml), dried with $MgSO_4$, filtered, and the solvent evaporated. FC (200 g 0.015-0.040 mm-$SiO_2$, flow: 60 ml/min., hexane/methyl t-butyl ether 100:0 to 85:15 in 30 min.) of the crude product (2.4 g) gave (3S,3aS,5R)-3,8-dimethyl-5-(prop-1-en-2-yl)-3,3a,4,5,6,7-hexahydroazulen-1(2H)-one (130 mg, 4%).
$^{13}$C-NMR (125 MHz, $C_6D_6$): δ 205.1 (s, C(1)), 153.2 (s, C(8)), 150.9 (s, C(2')), 137.2 (s, C(8a)), 109.1 (t, C(1')), 49.7 (d, C(5)), 48.0 (t, C(2)), 44.8 (d, C(3a)), 37.1 (t, C(7)), 32.9 (t, C(4)), 31.8 (d, C(3)), 30.2 (t, C(6)), 21.4 (q, MeC(8)), 21.0 (q, C(3')), 15.9 (q, MeC(3)).
MS (EI): 219 (7), 218 (41), 204 (8), 203 (51), 190 (5), 185 (6), 175 (20), 163 (10), 162 (20), 161 (40), 150 (20), 149 (12), 148 (15), 147 (27), 135 (20), 134 (12), 133 (42), 121 (33), 120 (85), 119 (51), 109 (30), 108 (100), 107 (83), 106 (22), 105 (67), 95 (60), 94 (14), 93 (66), 92 (16), 91 (79), 81 (20), 80

(20), 79 (63), 78 (12), 77 (51), 69 (30), 67 (40), 65 (26), 55 (42), 53 (36), 43 (17), 41 (65), 39 (35).

B) (1R,3S,3aS,5R)- and (1S,3S,3aS,5R)-3,8-dimethyl-5-(prop-1-en-2-yl)-1,2,3,3a,4,5,6,7-octahydroazulen-1-ol At −10° C., a mixture of (3S,3aS,5R)-3,8-dimethyl-5-(prop-1-en-2-yl)-3,3a,4,5,6,7-hexahydroazulen-1(2H)-one (53 mg, 0.243 mmol) and CeCl$_3$.7H$_2$O (90 mg, 0.243 mmol) in MeOH (5 ml) was treated with sodium borohydride (9.2 mg, 0.243 mg) and the resulting mixture was stirred at 0° C. for 20 min., poured into aqueous saturated NH$_4$Cl solution (5 ml) and ice and extracted twice with diethyl ether (3 ml). The combined organic phases were washed with aqueous saturated NaHCO$_3$ solution (3 ml), with aqueous saturated NaCl solution (3 ml), dried with MgSO$_4$, filtered, and the solvent evaporated. FC (5 g SiO$_2$, hexane/MTBE 10:0.1 to 10:0.2 to 10:0.5) of the crude product (52 mg, GC: 93:7 (1R)/(1S)-epimer) gave (1R,3S,3aS,5R)-3,8-dimethyl-5-(prop-1-en-2-yl)-1,2,3,3a,4,5,6,7-octahydroazulen-1-ol (34 mg, 64%) and (1 S,3S,3aS,5R)-3,8-dimethyl-5-(prop-1-en-2-yl)-1,2,3,3a,4,5,6,7-octahydroazulen-1-ol (1 mg, 2%).

I) (1R,3S,3aS,5R)-3,8-dimethyl-5-(prop-1-en-2-yl)-1,2,3,3a,4,5,6,7-octahydroazulen-1-ol $^{13}$C-NMR (125 MHz, C$_6$D$_6$): δ 151.67 (s, C(2')), 145.01 (s, C(8a)), 135.22 (s, C(8)), 108.51 (t, C(1')), 73.69 (d, C(1)), 51.02 (d, C(5)), 46.28 (d, C(3a)), 43.26 (t, C(2)), 36.03 (d, C(3)), 35.41 (t, C(7)), 33.70, 31.83 (2 t, C(4), C(6)), 21.78, 20.70, 16.72 (3 q, C(3'), MeC(3), MeC(8)).
MS (EI, polar column VF-WAX): 221 (4), 220 (27), 205 (13), 202 (14), 187 (17), 177 (11), 164 (21), 163 (32), 159 (11), 151 (12), 149 (18), 147 (12), 145 (17), 138 (23), 137 (20), 133 (19), 131 (13), 124 (13), 123 (32), 122 (13), 121 (29), 120 (22), 119 (38), 110 (21), 109 (45), 108 (100), 107 (58), 105 (31), 97 (15), 95 (50), 93 (40), 91 (32), 81 (25), 79 (26), 77 (20), 69 (21), 67 (24), 65 (8), 55 (31), 53 (15), 43 (21), 41 (39), 39 (13).
Odour description: woody.

II) (1S,3S,3aS,5R)-3,8-dimethyl-5-(prop-1-en-2-yl)-1,2,3,3a,4,5,6,7-octahydroazulen-1-ol $^{13}$C-NMR (125 MHz, C$_6$D$_6$): δ 151.88 (s, C(2')), 146.61 (s, C(8a)), 135.79 (s, C(8)), 108.84 (t, C(1')), 72.06 (d, C(1)), 51.72 (d, C(5)), 45.16 (d, C(3a)), 43.26 (t, C(2)), 35.20 (d, C(3)), 35.01 (t, C(7)), 31.67, 31.43 (2 t, C(4), C(6)), 21.59, 20.86, 15.54 (3 q, C(3'), MeC(3), MeC(8)).
MS (EI, polar column VF-WAX): 221 (11), 220 (73), 205 (29), 202 (13), 191 (9), 187 (22), 177 (34), 164 (26), 163 (64), 159 (25), 151 (27), 150 (13), 149 (31), 147 (14), 146 (13), 145 (33), 138 (26), 137 (57), 133 (35), 131 (25), 125 (19), 124 (21), 123 (48), 122 (17), 121 (42), 120 (35), 119 (52), 111 (23), 110 (34), 109 (62), 108 (85), 107 (98), 106 (16), 105 (54), 97 (26), 95 (100), 93 (56), 91 (50), 81 (40), 79 (41), 77 (34), 69 (33), 67 (37), 65 (12), 55 (50), 53 (25), 43 (32), 41 (65), 39 (19).
Odour description: woody.

EXAMPLE 3

Mixture of (1R,3S,5R,8S)-/(1S,3S,5R,8S)-3,8-dimethyl-5-(prop-1-en-2-yl)-1,2,3,4,5,6,7,8-octahydroazulen-1-ol and rotundone from an olefinic mixture containing α-guaiene Composition (% w/w) of the starting olefinic mixture according to GC-MS analysis: δ-elemene (0.3), β-patchoulene (5.6), β-elemene (3), cycloseychellene (1.75), β-caryophyllene (7), α-guaiene (27), α-patchoulene (10), seychellene (14), δ-patchoulene (5.5), γ-patchoulene (0.45), α-humulene (1), aciphyllene (4), α-bulnesene (18).
A mixture of alpha-guaiene rich olefinic fraction (200 g), 1M KH$_2$PO$_4$/K$_2$HPO$_4$ pH 7.5 buffer solution (200 ml), DeniLite® II S laccase (20 g; from Novozymes), and water (1600 ml) was stirred vigorously while a slow flow of air was bubbled through the sintered glass end of a gas introduction tube, and heated at 40° C. for 46 hours. Air-bubbling was stopped and NaOH (20 g, 0.5 mol) was added into the mixture that was heated to reflux under vigorous stirring and N$_2$-bubbling for 9.5 h while the colour of the mixture turned from yellow to brown The resulting mixture was cooled to 25°, poured into H$_2$O (750 ml), and extracted twice with MTBE (750 and 350 ml). The joined organic phases were washed twice with H$_2$O (250 ml) and once with aqueous saturated NaCl solution (250 ml), and dried with MgSO$_4$. Filtration and evaporation of the solvent led to 188 g of crude material. Short-path distillation led to 55.5 g (28% yield based on 200 g olefinic mixture) of olfactorily pure material (fractions 8-15, 104-153° C./0.10 mbar, oil bath temperature 125-175° C.).
GC-analysis: 7.0% caryophyllene oxide, 2.9% (1R,3S,5R, 8S)-3,8-dimethyl-5-(prop-1-en-2-yl)-1,2,3,4,5,6,7,8-octahydroazulen-1-ol, 3.1% (1S,3S,5R,8S)-epimer, 4.2% β-patchoulenone, 7.2% rotundone, 0.3% α-bulnesenone, 0.5% (1R,3S,3aS,5R)-3,8-dimethyl-5-(prop-1-en-2-yl)-1,2,3,3a,4,5,6,7-octahydroazulen-1-ol (compound of formula I), 0.9% (1 S,3S,3aS,5R)-3,8-dimethyl-5-(prop-1-en-2-yl)-1,2,3,3a,4,5,6,7-octahydroazulen-1-ol (compound of formula I).
Odour description of the mixture (fraction 8-15): woody, floral, tobacco, reminiscent of some aspects of patchouli and pepper.

EXAMPLE 4

Composition Obtained from α-Bulnesene-Rich Olefinic Fraction

Composition (% w/w) of the starting olefinic mixture according to GC-MS analysis: α-guaiene (0.7), α-patchoulene (4.5), seychellene (2.8), δ-patchoulene (1.7), γ-patchoulene (1.1), α-humulene (0.4), aciphyllene (14), α-bulnesene (66).
A mixture of alpha-bulnesene rich olefinic fraction (400 g), 1M KH$_2$PO$_4$/K$_2$HPO$_4$ pH 7.5 buffer solution (200 ml), DeniLite® II S laccase (20 g), and water (1400 ml) was stirred vigorously while a slow flow of air was bubbled through the sintered glass end of a gas introduction tube, and heated at 40° C. for 68 hours. Air-bubbling was stopped and NaOH (20 g, 0.5 mol) was added into the mixture that was heated to reflux under vigorous stirring and N$_2$-bubbling for 9 h while the colour of the mixture turned from yellow to brown The resulting mixture was cooled to 25°, poured into H$_2$O (1500 ml), and extracted twice with MTBE (1500 and 750 ml). The joined organic phases were washed with H$_2$O (500 ml) and with aqueous saturated NaCl solution (500 ml), and dried with MgSO$_4$. Filtration and evaporation of the solvent led to 406 g of crude material. Short-path distillation led to 181 g (45% yield based on 400 g olefinic mixture) of olfactorily pure material (fractions 7-16, 108-160° C./0.06 mbar, oil bath temperature 140-200° C.).
GC-analysis: 15% α-bulnesene oxides, 1%/3-patchoulenone, 1.25% rotundone, 1.8% bulnesenone, 0.1% (1R,3S, 3aS,5R)-3,8-dimethyl-5-(prop-1-en-2-yl)-1,2,3,3a,4,5,6,7-octahydroazulen-1-ol (compound of formula I), 1.6% (1S,3S, 3aS,5R)-3,8-dimethyl-5-(prop-1-en-2-yl)-1,2,3,3a,4,5,6,7-octahydroazulen-1-ol (compound of formula I).

Odour description of the mixture (fraction 7-16): woody, tobacco, reminiscent of some aspects of patchouli and pepper.

EXAMPLE 5

Mixture of (1R,3S,5R,8S)-/(1S,3S,5R,8S)-3,8-dimethyl-5-(prop-1-en-2-yl)-1,2,3,4,5,6,7,8-octahydroazulen-1-ol and (−)-rotundone from an olefinic mixture enriched in α-guaiene Composition (% MO) of the starting olefinic mixture according to GC-MS analysis: 8-elemene (0.14), β-patchoulene (3.8), cycloseychellene (2.3), β-caryophyllene (12), α-guaiene (49), α-patchoulene (11), seychellene (14.5), aciphyllene (0.2), α-bulnesene (0.4).

A mixture of alpha-guaiene rich olefinic fraction (500 g), 1M $KH_2PO_4/K_2HPO_4$ pH 7.5 buffer solution (200 ml), DeniLite® II S laccase (20 g), and water (1300 ml) was stirred vigorously while a slow flow of air was bubbled through the sintered glass end of a gas introduction tube, and heated at 40° C. for 69 hours. Air-bubbling was stopped and NaOH (20 g, 0.5 mol) was added into the mixture that was heated to reflux under vigorous stirring and $N_2$-bubbling for 8 h while the colour of the mixture turned from yellow to brown The resulting mixture was cooled to 25°, poured into $H_2O$ (1500 ml), and extracted twice with MTBE (1500 and 1000 ml). The joined organic phases were washed twice with $H_2O$ (500 ml) and once with aqueous saturated NaCl solution (500 ml), and dried with $MgSO_4$. Filtration and evaporation of the solvent led to 493 g of crude material. Short-path distillation led to 140 g (28% yield based on 500 g olefinic mixture) of olfactorily pure material (fractions 6-13, 105-147° C./0.05 mbar, oil bath temperature 130-180° C.).

GC-analysis: 15.0% caryophyllene oxides, 5.4% (1R,3S,5R,8S)-3,8-dimethyl-5-(prop-1-en-2-yl)-1,2,3,4,5,6,7,8-octahydroazulen-1-ol, 4.5% (1 S,3S,5R,8S)-epimer, 2.7%/3-patchoulenone, 12.9% rotundone.

Odour description of the mixture (fraction 6-13): woody, floral, tobacco, reminiscent of some aspects of patchouli and pepper.

EXAMPLE 6

Mixture of (1R,3S,5R,8S)-/(1S,3S,5R,8S)-3,8-dimethyl-5-(prop-1-en-2-yl)-1,2,3,4,5,6,7,8-octahydroazulen-1-ol and (−)-rotundone from patchouli oil Composition (% w/w) of the starting olefinic mixture according to GC-MS analysis: β-patchoulene (2), β-caryophyllene (3), α-guaiene (16), α-patchoulene (6.5), seychellene (7), α-bulnesene (20), patchoulol (38).

A mixture of patchouli iron free Indonesia (200 g), 1M $KH_2PO_4/K_2HPO_4$ pH 7.5 buffer solution (200 ml), DeniLite® II S laccase (20 g), and water (1600 ml) was stirred vigorously while a slow flow of air was bubbled through the sintered glass end of a gas introduction tube, and heated at 40° C. for 52 hours. Air-bubbling was stopped and NaOH (20 g, 0.5 mol) was added into the mixture that was heated to reflux under vigorous stirring and $N_2$-bubbling for 9 h while the colour of the mixture turned from yellow to brown The resulting mixture was cooled to 25°, poured into $H_2O$ (1500 ml), and extracted twice with MTBE (1500 and 750 ml). The joined organic phases were washed twice with $H_2O$ (500 ml) and once with aqueous saturated NaCl solution (500 ml), and dried with $MgSO_4$. Filtration and evaporation of the solvent led to 196 g of crude material. Short-path distillation led to 47 g (23% yield based on 200 g olefinic mixture) of olfactorily pure material (fractions 8-13, 100-135° C./0.12 mbar, oil bath temperature 130-180° C.).

GC-analysis: 1% α-bulnesene oxides, 1.8% β-patchoulenone, 2.7% rotundone, 62% patchoulol ((1R,4S,4aS,6R,8aS)-octahydro-4,8a,9,9-tetramethyl-1,6-methanonaphthalen-1(2H)-ol)

Odour description of the mixture (fraction 8-13): woody, earthy, floral, tobacco.

EXAMPLE 7

Perfuming Composition

| Ingredients | parts by weight 1/900 |
|---|---|
| Alpha Hexyl Cinnamic Aldehyde | 80 |
| Bergamot Essential Oil from Italy | 250 |
| Cardamom Seed Essential Oil | 3 |
| Cedryl Methyl Ether [1] | 120 |
| Coriander Seed Essential Oil | 13 |
| Coumarin | 20 |
| Cyclohexal (4-(4-hydroxy-4-methylpentyl)cyclohex-3-enecarbaldehyde) | 65 |
| Hedione (methyl 2-(3-oxo-2-pentylcyclopentyl)acetate) | 150 |
| Methyl Cedryl Ketone [2] | 110 |
| Rose Oxide (4-methyl-2-(2-methylprop-1-enyl)tetrahydro-2H-pyran) 10%/DPG | 3 |
| Sandalore(3-methyl-5-(2,2,3-trimethylcyclopent-3-enyl)pentan-2-ol) | 20 |
| Vanillin | 6 |
| Mixture obtained according to Example 3 | 60 |

[1] (3R,3aS,6R,7R,8aS)-octahydro-6-methoxy-3,6,8,8-tetramethyl-1H-3a,7-methanoazulene
[2] 1-[(3R,3aR,7R,8aS)-2,3,4,7,8,8a-hexahydro-3,6,8,8-tetramethyl-1H-3a,7-methanoazulen-5-yl]-ethanone The addition of the mixture obtained according to the procedure described in Example 3 imparts to the perfume composition, on the one hand a woody, balsamic, peppery note reminding of some cedar aspects of patchouli and of some tobacco-like aspects of agarwood and on the other hand a floral, rosy note reminding of dried leaves. Moreover, the addition of the mixture of Example 3 boosts the bergamot-coumarine accord thus enhancing the diffusion, volume and trail of the whole fragrance.

EXAMPLE 8

Fragrance Composition for e.g. Shower Gel

| Ingredients | parts by weight 1/1000 |
|---|---|
| Cis-3-Hexenyl Acetate | 2 |
| Terpinyl Acetate (2-(4-methylcyclohex-3-enyl)propan-2-yl acetate) | 60 |
| Agrumex (2-(1,1-dimethylethyl)-cyclohexanol acetate) | 50 |
| Alpha-Hexyl Cinnamic Aldehyde (2-(phenylmethylene)-octanal) | 60 |
| Decylic Aldehyde (C10 Aldehyde) | 1 |
| Allyl Amyl Glycolate (allyl 2-(isopentyloxy)acetate) | 4 |
| Citronellol | 80 |

13
-continued

| Ingredients | parts by weight 1/1000 |
|---|---|
| Beta Damascone | 1 |
| Dihydromyrcenol | 60 |
| Florhydral (3-(3-isopropylphenyl)-butanal) | 3 |
| Fructone (2-methyl(1,3-dioxolane-2-acetic acid)-ethyl ester) | 20 |
| Galaxolide[(1)] | 100 |
| Geraniol | 150 |
| Hedione (3-oxo-2-pentyl(cyclopentaneacetic acid)methyl ester) | 50 |
| Beta Ionone | 15 |
| Lilial (4-(1,1-dimethylethyl)-alpha-methyl-benzenepropanal) | 50 |
| Linalol (3,7-dimethyl-(octa-1,6-dien-3-ol)) | 150 |
| Manzanate (ethyl 2-methylpentanoate) | 4 |
| Pharaone (2-cyclohexyl-1,6-heptadiene-3-one) 10%/DPG | 3 |
| Pomarose ® (5,6,7-trimethylocta-2,5-dien-4-one) 10%/DPG | 4 |
| Hexyl Salicylate | 80 |
| Mandarine Essential Oil | 30 |
| Tricyclal (2,4-dimethyl-(3-cyclohexene-1-carboxaldehyde)) | 1 |
| Violet Nitrile (2,6-nonadienenitrile) 10%/TEC at 1%/DPG | 2 |
| Title compounds of Example 1 | 20 |

[(1)]1,3,4,6,7,8-hexahydro-4,6,6,7,8,8-hexamethyl-cyclopenta[g]-2-benzopyran

The addition of the one of the title compounds of the Example 1 (i.e. (1R,3S,5R,8S)- or (1S,3S,5R,8S)-3,8-dimethyl-5-(prop-1-en-2-yl)-1,2,3,4,5,6,7,8-octahydroazulen-1-ol) or of a mixture thereof imparts a natural, floral, rosy note to the composition and a fruity connotation reminding of raspberries.

EXAMPLE 9

Flavour Composition

| Ingredients | parts by weight 1/1000 |
|---|---|
| Propylene Glycol | 978.7245 |
| Vanillin | 2.040816 |
| Maltol (3-hydroxy-2-methyl-4H-pyran-4-one) | 5.102041 |
| Raspberry Ketone (4-(4-methoxyphenyl)-butan-2-one) | 12.244898 |
| Ethyl Vanillin | 1.020408 |
| Iso-Butyl Acetate | 0.051020 |
| Irone Alpha (4-(2,5,6,6-tetramethyl-2-cyclohexen-1-yl)-3-buten-2-one) | 0.816327 |

An 0.08 weight % aqueous solution of the raspberry flavour described above was prepared and the effect of the addition of 0.001 ppm of fraction 8-15 obtained according to Example 3 was evaluated.

The addition of the mixture obtained according to Example 3 brings a unique and natural touch to the composition, complexity, seedy and ripe effects reminding of wild-type raspberries. A similar effect was observed when the content of the mixture obtained according to Example 3 was lowered to 0.0001 ppm.

14

The invention claimed is:

1. A process of producing a compound of formula (I)

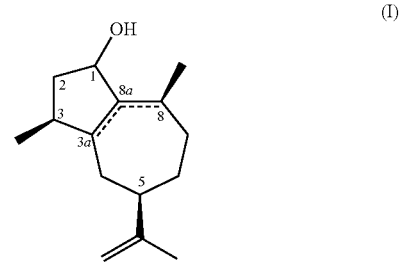

wherein the dotted line together with the carbon-carbon bond between C-3a and C-8a represents a double bond and the dotted line together with carbon-carbon bond between C-8a and C-8 represents a single bond, and C-3 and C-8 are (S)-configurated, and C-5 is (R)-configurated; or the dotted line together with the carbon-carbon bond between C-8 and C-8a represents a double bond and the dotted line together with carbon-carbon bond between C-3a and C-8a represents a single bond, and C-3 and C-3a are (S)-configurated, and C-5 is (R)-configurated;

by reacting laccase and a material comprising α-guaiene and/or α-bulnesene in the presence of an oxygen source to form the compound of formula (I).

2. The process according to claim 1 wherein the material is patchouli oil.

3. The process according to claim 2 wherein the light fraction of patchouli oil is used.

4. The process according to claim 3 wherein the light fraction of patchouli oil is essentially free of patchouli alcohol.

5. The process according to claim 1 wherein the reaction takes place in the presence of a mediator to enhance the reaction.

6. The process according to claim 1 wherein air is used as oxygen source.

7. A compound of formula (I)

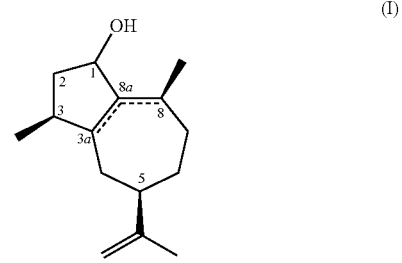

wherein the dotted line together with the carbon-carbon bond between C-3a and C-8a represents a double bond and the dotted line together with carbon-carbon bond between C-8a and C-8 represents a single bond, and wherein C-3 and C-8 are (S)-configurated, and C-5 is (R)-configurated.

8. A flavour or fragrance composition comprising a compound of formula (I)

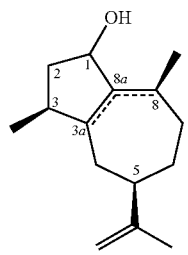

(I)

wherein the dotted line together with the carbon-carbon bond between C-3a and C-8a represents a double bond and the dotted line together with carbon-carbon bond between C-8a and C-8 represents a single bond, and C-3 and C-8 are (5)-configurated, and C-5 is (R)-configurated; or the dotted line together with the carbon-carbon bond between C-8 and C-8a represents a double bond and the dotted line together with carbon-carbon bond between C-3a and C-8a represents a single bond, and C-3 and C-3a are (S)-configurated, and C-5 is (R)-configurated;

obtainable through the process by reacting patchouli oil or a light fraction of patchouli oil and laccase in the presence of an oxygen source.

9. A flavour or fragrance application comprising
a) a compound of formula (I)

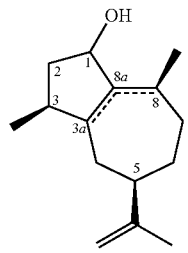

(I)

wherein the dotted line together with the carbon-carbon bond between C-3a and C-8a represents a double bond and the dotted line together with carbon-carbon bond between C-8a and C-8 represents a single bond, and C-3 and C-8 are (S)-configurated, and C-5 is (R)-configurated; or the dotted line together with the carbon-carbon bond between C-8 and C-8a represents a double bond and the dotted line together with carbon-carbon bond between C-3a and C-8a represents a single bond, and C-3 and C-3a are (5)-configurated, and C-5 is (R)-configurated; and b) a consumer product base.

10. A method of manufacturing the flavour or fragrance application of claim 9, comprising incorporating the compound of formula (I) in the application, either
a) by directly admixing the compound of formula (I) to the consumer product base, or
b) by admixing a flavour/fragrance composition comprising the compound of formula (I), which composition is then mixed with the consumer product base.

* * * * *